(12) United States Patent
Feygin et al.

(10) Patent No.: US 6,890,491 B1
(45) Date of Patent: May 10, 2005

(54) METHOD AND APPARATUS FOR UNIVERSAL FLUID EXCHANGE

(75) Inventors: Ilya Feygin, Mountainside, NJ (US); Rhett L. Affleck, Lawrenceville, NY (US); Leslie A. Walling, Somerset, NJ (US); Peter Kieselbach, Upper Black Eddy, PA (US); Gregory Louis Kirk, Skillman, NJ (US); Ian Henderson, Hopewell, NJ (US)

(73) Assignee: Pharmacopeia Drug Discovery, Inc., Cranbury, NJ (US)

( * ) Notice: Subject to any disclaimer, the term of this patent is extended or adjusted under 35 U.S.C. 154(b) by 608 days.

(21) Appl. No.: 08/872,097

(22) Filed: Jun. 10, 1997

(51) Int. Cl.[7] ................................................ B01J 19/00
(52) U.S. Cl. ..................... 422/130; 422/100; 422/102; 422/129; 422/131; 436/177; 436/180
(58) Field of Search ...................... 422/130, 63, 64, 422/49, 100, 101, 102, 104, 131, 135, 136, 138; 436/43, 174, 177, 180

(56) References Cited

U.S. PATENT DOCUMENTS

| | | | | |
|---|---|---|---|---|
| 3,557,077 A | * | 1/1971 | Brunfeldt et al. ............ | 422/134 |
| 3,647,390 A | * | 3/1972 | Kubodera et al. ........... | 422/134 |
| 3,715,190 A | * | 2/1973 | Park et al. .................... | 422/131 |
| 4,748,002 A | * | 5/1988 | Neimark et al. .............. | 422/116 |
| 5,039,488 A | * | 8/1991 | Kohr ............................. | 422/68.1 |
| 5,053,454 A | * | 10/1991 | Judd ........................... | 525/54.11 |
| 5,147,551 A | * | 9/1992 | Averette ...................... | 210/640 |
| 5,171,531 A | | 12/1992 | Christianson et al. .......... | 422/64 |
| 5,173,188 A | * | 12/1992 | Winter et al. ................ | 210/634 |
| 5,193,703 A | * | 3/1993 | Staats, III et al. ........... | 220/203 |
| 5,223,435 A | * | 6/1993 | Kohr ............................ | 436/89 |
| 5,260,028 A | * | 11/1993 | Astle ............................ | 422/81 |
| 5,286,652 A | | 2/1994 | James et al. ................... | 436/48 |
| 5,316,728 A | * | 5/1994 | Hayashi et al. ............... | 422/70 |
| 5,350,565 A | | 9/1994 | Leveson et al. .............. | 422/64 |
| 5,380,495 A | * | 1/1995 | Chang et al. ................. | 422/131 |
| 5,503,805 A | * | 4/1996 | Sugarman et al. ........... | 422/131 |
| 5,514,336 A | | 5/1996 | Fox .............................. | 422/64 |
| 5,565,324 A | | 10/1996 | Still et al. ....................... | 435/6 |
| 5,585,068 A | | 12/1996 | Panetz et al. ................. | 422/64 |
| 5,660,727 A | * | 8/1997 | Gleave et al. .............. | 210/141 |
| 5,888,830 A | * | 3/1999 | Mohan et al. .............. | 436/174 |
| 6,126,904 A | * | 10/2000 | Zuellig et al. .............. | 422/130 |

OTHER PUBLICATIONS

Desai et al. "Recent Advances in the Generation of Chemical Diversity Libraries", Drug Development Research, vol. 33, pp. 174–188, 1994.

(Continued)

*Primary Examiner*—Jill Warden
*Assistant Examiner*—Dwayne K. Handy
(74) *Attorney, Agent, or Firm*—Priest & Goldstein, PLLC

(57) ABSTRACT

A universal fluid exchange device includes upper and lower reaction vessel supports which include pressure sealed injection and evacuation ports for each supported reaction vessel. Reaction vessels matingly engage through the injection and evacuation ports with fittings which are connected through flexible tubing to respective supplying and receiving vessels. The reaction vessels or fittings are moved into position, as required, so that reactants may be directly supplied from supplying vessels in the order and amount desired without operation of valves that can become contaminated, and so that the reaction vessels may dispel their contents into the appropriate receiving vessels. The system may be highly advantageous in applications such as combinatorial chemistry where myriad combinations of chemicals, solvents and reagents are employed.

42 Claims, 7 Drawing Sheets

OTHER PUBLICATIONS

Pavia et al. "The Generation of Molecular Diversity", Bioorganic & Medicinal Chemistry Letters, vol. 3, No. 3, pp. 387–396, 1993.

Galloop et al. "Applications of Combinatorial Technologies to Drug Discovery. 1. Background and Peptide Combinatorial Libraries", Journal of Medicinal Chemistry, vol. 37, No. 9, pp. 1234–1251, Apr. 29, 1994.

Gordon et al. "Applications of Combinatorial Technologies to Drug Discovery. 2. Combinatorial Organic Synthesis, Library Screening Strategies, and Future Directions", Journal of Medicinal Chemistry, vol. 37, No. 10, pp. 1385–1401, 1994.

* cited by examiner

METHOD AND APPARATUS FOR UNIVERSAL FLUID EXCHANGE

BACKGROUND OF THE INVENTION

1. Field of the Invention

The present invention is related generally to the manipulation of fluids and reaction vessels for improved universal fluid exchange and, more specifically, to delivery methods and systems which provide fluids to and evacuate fluids from reaction vessels, as well as to provide individual control of heating and stirring in the reaction vessels.

2. Description of the Related Art

The ability to appropriately manipulate reaction vessels for a plurality of parallel chemical reactions and to provide and evacuate fluids from such vessels is becoming increasingly important. As the number of desired chemical reactions increases, manual or simple mechanical arrangements become impractical. By way of example, combinatorial chemical synthesis permits the production of very large numbers of small molecule chemical compounds which may, for example, be tested for biological activity.

One combinatorial synthesis method employs polymeric resin beads as solid phase substrates upon which the small molecule compounds are formed. In this method, sometimes referred to as the "mix and split" method, a sample of beads is divided among several reaction vessels and a different reaction is performed in each vessel. The beads from all the vessels are then pooled and redivided into a second set of vessels, each of which now contains approximately equal numbers of beads carrying the products of the first set of reactions. When a second reaction is performed, each of the products of the first set of reactions acts as a substrate for a new set of reactions which produce all the possible combinations of reaction products.

The mix and split combinatorial chemical synthesis method is discussed in greater detail in, M. A. Gallop, R. W. Barrett, W. J. Dower, S. P. A. Fodor and E. M. Gordon, Applications of Combinatorial Technologies to Drug Discovery, 1. Background and Peptide Combinatorial Libraries, Journal of Medical Chemistry 1994, Vol. 37, pp. 1233–1251; E. M Gordon, R. W. Barrett, W. J. Dower, S. P. A. Fodor and M. A. Gallop, Applications of Combinatorial Technologies to Drug Discovery, 2. Combinatorial organic Synthesis, Library Screening Strategies and Future Directions, Journal of Medical Chemistry 1994, Vol. 37, pp.1385–1401, M. R. Pavia, T. K. Sawyer, W. H. Moos, The Generation of Molecular Diversity, Bioorg. Med. Chem. Lett. 1993, Vol. 3, pp. 387–396 and M. C. Desai, R. N. Zuckerman and W. H. Moos, Recent Advances in the Generation of Chemical Diversity Libraries, Drug co Dev. Res. 1994, Vol. 33, pp. 174–188 which are hereby Co incorporated by reference. See also, U.S. Pat. No. 5,565,324 which is also hereby incorporated by reference.

By providing an extremely large library of chemical compounds for testing, combinatorial chemical synthesis provides support for the development of compounds which may be used to develop new drugs for treating a wide range of diseases. Rather than painstakingly manually synthesizing chemicals one at a time and individually testing them for biological activity with, for example, an enzyme involved in heart disease, or a cell receptor involved in fighting cancer, many chemicals can be developed and tested in parallel, greatly accelerating the drug development process and, hopefully, leading to major advances in the treatment and prevention of disease.

Unfortunately, the task of simultaneously synthesizing a large number of compounds can involve complex, unwieldy processes and equipment. Generally, reagents and solvents must be added to reaction vessels in precisely timed sequences. Additionally, the temperature of each reaction vessel must often be well-defined and a specific temperature profile may be required for optimal reaction. Typically, the contents of each reaction vessel should be stirred or mixed in order to ensure the proper distribution of reactants.

One conventional approach to delivering fluids to reaction vessels relies upon a labyrinthine plumbing system which routes solvents, reactants and reagents to various reaction vessels through tubes selected by a complex valving system which may be under computer control. A similar system is required to remove the reaction products from vessels. Not only is such a system complex and expensive, it also presents major maintenance, reliability and contamination problems.

For example, all the tube material and the valves which direct flow among the tubes must be maintained on a regular basis. The valve materials may be corroded or otherwise damaged by contact with the reagents, solvents or reaction products and consequently must be vigilantly maintained in order to prevent cross-contamination. Even if the valves and tubes are well-maintained, in light of the diverse range of chemicals that may be involved, there is still a very real threat of corrosion and cross-contamination. Additionally, controlling the timing, mixing, and heating of reactants within such a complex system is a formidable task and, with conventional mixing systems, the beads which provide reaction surfaces are often ground up to some extent against the bottom of the reaction vessel.

In order to reduce the complex plumbing of valve and tube systems, some systems rely upon robotic arms to deliver reagents into reaction vessels under program control. Although the complexity of the plumbing system is greatly reduced in these systems, the robotic system is highly complex and subject to its own problems. Regular maintenance is required on such systems, spills are an inherent hazard, contamination remains a problem, and it may be difficult to control the temperature of and to provide proper agitation for reactants.

Additionally, both the typical valve and tube systems and the robot arm systems tend to be large and expensive. Consequently they are not ideally suited for the every day use of a synthetic chemist.

Similar issues, as those discussed above, arise in a variety of contexts where multiple processes are employed with multiple reaction vessels. For example, chemical synthesis in general, tagging and tag washing, solvent exchangers and bead washers may all be improved utilizing the approaches of the present invention which are described below.

SUMMARY OF THE INVENTION

The present invention is directed to methods and apparatus for simply and cost effectively achieving universal fluid exchange and manipulating one or more reaction vessels. The invention may suitably be employed in combinatorial chemical synthesis reaction systems which are simple, low cost and highly reliable, but will be applicable in a wide variety of contexts. Methods and apparatus in accordance with the present invention may reduce the likelihood of spills and of cross contamination, provide for the effective individual heating of reaction vessels, and supply effective agitation of reactants without substantially grinding up internal particles, such as the microscopic beads which support the chemical compounds in combinatorial chemical synthesis, thereby increasing the yield of the synthesis.

In one aspect, the invention may comprise upper and lower reaction vessel supports which include pressure sealed injection and evacuation ports for each supported reaction vessel. Reaction vessels matingly engage through the injection and evacuation ports with fittings which are connected through flexible tubing to respective supplying and receiving vessels. The reaction vessels, or fittings, are moved into position, as required, so that the reaction vessel may be supplied with reactants from supplying vessels in the order and amount desired and so that the reaction vessels may provide their contents to the appropriate receiving vessels. By moving the vessels, fluids may be supplied through dedicated supply lines which will not become contaminated as they will only deliver a single type of fluid. Also, no valves and no complicated tubing arrangements are necessary.

In another aspect, reaction vessels include intake and evacuation ports in their respective tops and bottoms and a ring of such reaction vessels is supported on a carousel which is controllably rotated. Top and bottom fitting carousels are stationary and the reaction vessel carousel rotates to mate the desired fittings to the respective reaction vessel ports. Seals may be made simply by clamping so that both vessel holding and vessel sealing to insure leak proof liquid injection and drainage are simply accomplished. Magnetic stirrers may be utilized to provide individually-controlled agitation for each reaction vessel. Spring-loaded resistive heating pads with inline sensing, wrapped around each reaction vessel, may be employed to control reaction temperature.

In a preferred embodiment a stirrer actuator and heating pad may be combined in an integral unit. These and other features, aspects and advantages of the invention will be apparent to those skilled in the art from the following detailed description, taken together with the accompanying drawings.

DETAILED DESCRIPTION

A universal fluid exchanger in accordance with the present invention is preferably simple, low cost and reliable. By comparison with conventional systems employed in combinatorial chemical syntheses, parallel chemical syntheses, and the like, it should preferably reduce the likelihood of spills and of cross contamination, provide for effective heating of reaction vessels, and supply effective agitation of reactants without grinding solid phase materials in the vessels, such as the microscopic beads which support the chemical compounds in combinatorial chemical reactions.

In one embodiment, the present invention may suitably comprise upper and lower reaction vessel supports which include pressure sealed injection and evacuation ports for each supported reaction vessel. Reaction vessels matingly engage through the injection and evacuation ports with fittings which are connected through flexible tubing to respective supplying and receiving vessels. In the presently preferred embodiments, these flexible tubes deliver fluids directly from a supply vessel to a reaction vessel without intervening valves. One suitable way of controlling this delivery of fluids is by pressurizing the supply vessels and controllably adjusting the pressure to control fluid delivery. It will be recognized that a variety of other techniques might also be employed.

The reaction vessels, or fittings, are preferably moved into position, as required, so that the reaction vessel may be supplied with reactants from the appropriate supplying vessel in the order and amount desired. As each delivery tube is dedicated to an associated supplying vessel, the risk of cross contamination is eliminated. Similarly, movement of the fittings or vessels permits proper alignment of the reaction vessels for drainage of the contents of the reaction vessels into receiving vessels.

Figure 1:
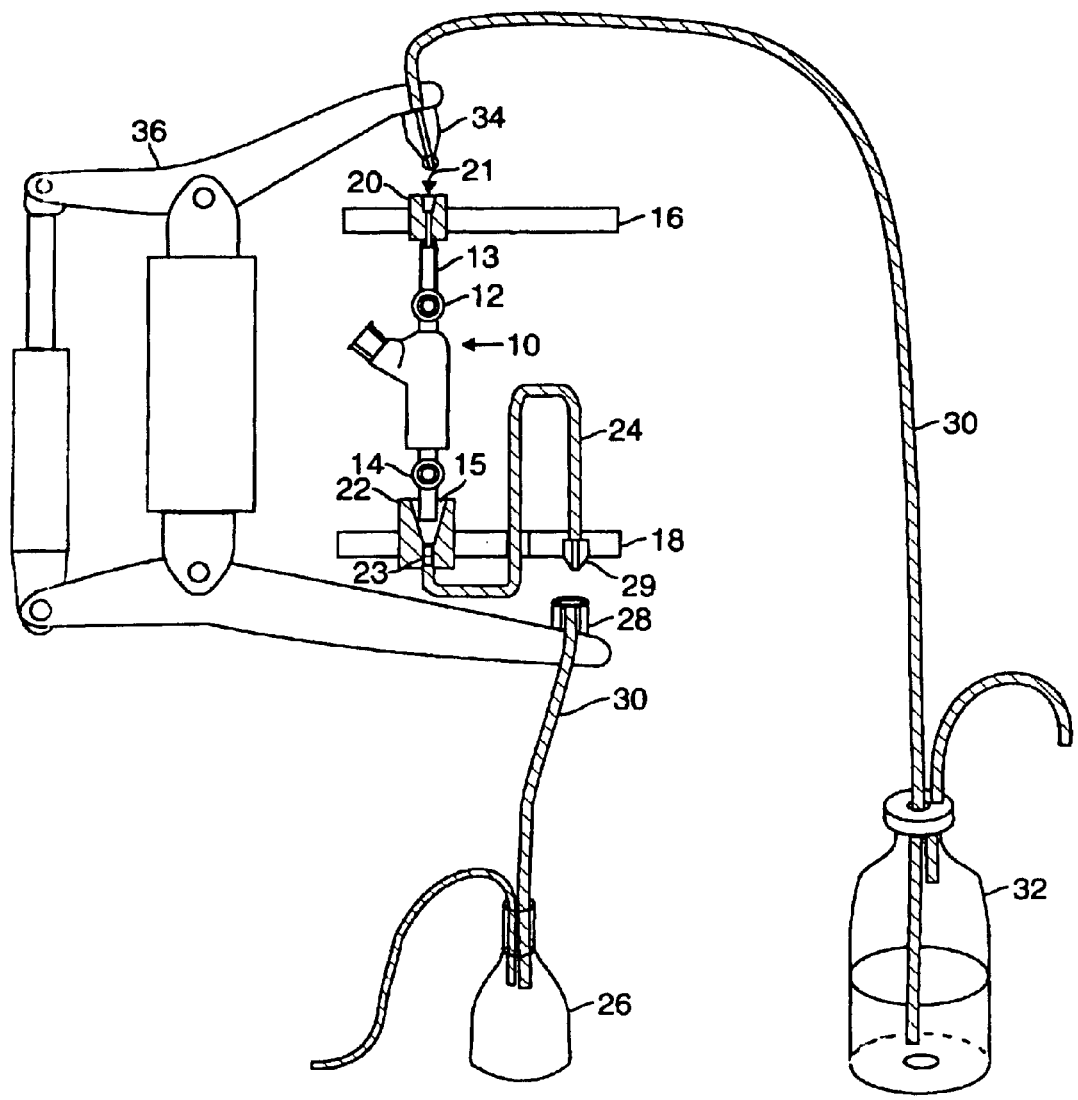
FIG. 1 illustrates the basic components of a universal fluid exchanger in accordance with the present invention.

As illustrated in FIG. 1, an embodiment of a universal fluid exchanger may suitably include a reaction vessel 10. While a single reaction vessel 10 is shown, it will be recognized that a plurality of vessels will typically be employed as discussed further below. A presently preferred vessel for use as the vessel 10 is described in greater detail in "A Solid Phase Synthesis Reaction Vessel and Method of Using Same," U.S. Pat. No. 5,851,494 and which is incorporated by reference herein. The vessel 10 may have top 12 and bottom 14 stop cocks, respectively which are preferably made of Teflon. Top and bottom glass tubes 13 and 15 of vessel 10 may be simply clamped into mounts 20 and 22, alternatively, spring loaded, or other fittings may be employed in the top and bottom. Chemically resistant O-rings, disposed at the ends of tubes 13 and 15 might also be used to facilitate the insertion or removal of the vessel 10. Respective top 16 and bottom 18 reaction vessel supports accommodate the reaction vessel 10. Injection 21 and evacuation 23 ports associated respectively with supports 16 and 18, communicate with vessel 10 through mounts 20 and 22, respectively. Ports 21 and 23 are preferably composed of a resilient material such as Teflon for pressure sealed access to the reaction vessel 10.

Figure 2B:
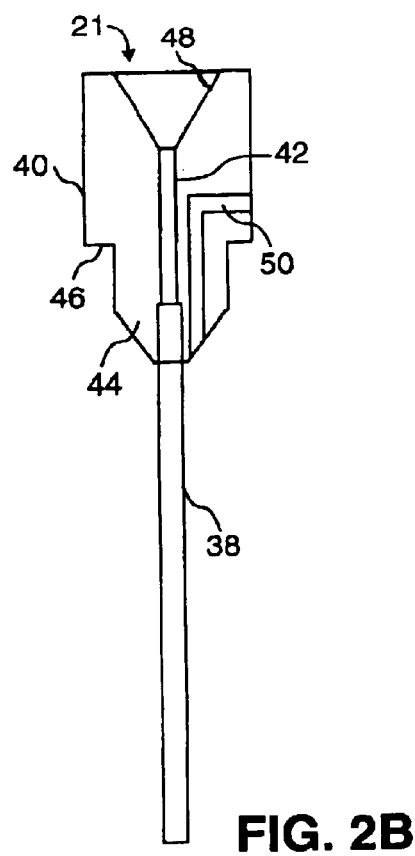
FIGS. 2B and 2C are sectional views of suitable reaction vessel injection and evacuation ports for the reaction vessel of FIG. 2A.
Figure 2A:
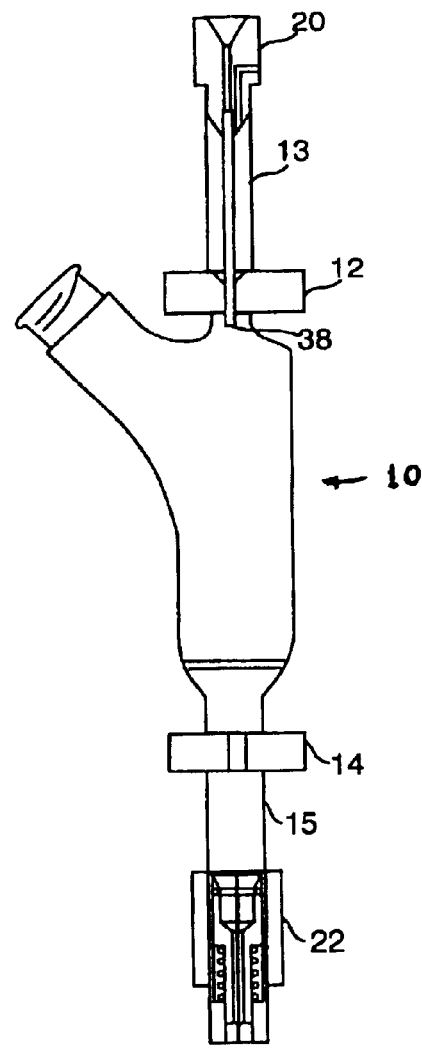
FIG. 2A illustrates a suitable reaction vessel for use in conjunction with the present invention.
Figure 2C:
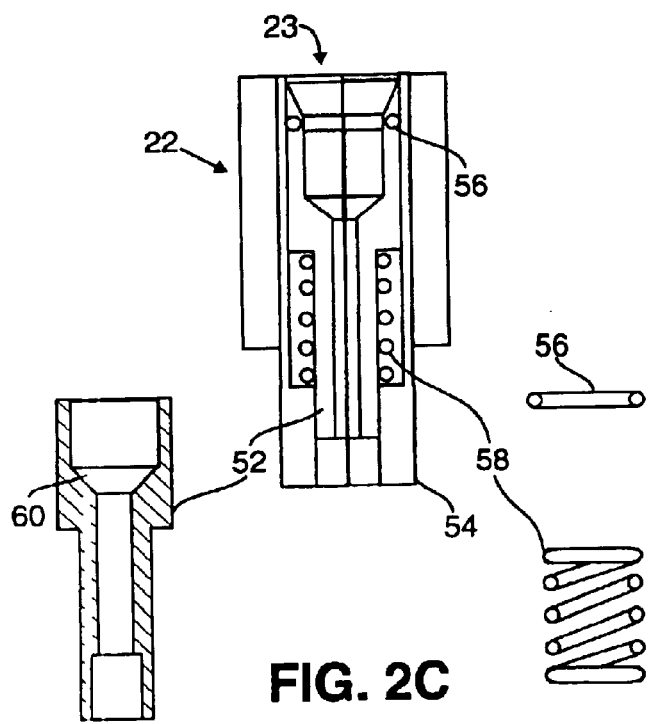

As described in greater detail in relation to the discussion of FIGS. 2B and 2C, the presently preferred injection port 21 includes a through fitting and top glass vessel tube 13, and the presently preferred evacuation port 23 includes a spring-loaded bottom through fitting and bottom glass vessel tube 15. In combination the spring loaded through fitting of the evacuation port 23 and the through fitting of the injection port 21 permit easy removal and replacement of the reaction vessel 10.

Each reaction vessel 10 preferably has an associated U-valve 24 composed of flexible non-reactive tubing such as standard commercially available Teflon tubing, which selectively shuts or opens the flow of materials from the reaction vessel 10 through the evacuation port 23 to a receiving vessel 26 which is connected to an evacuation fitting 28 through flexible tubing 30. The U-valve is shut when in a raised vertical position and open when in a horizontal position. The evacuation fitting 28 matingly engages with a through fitting 29 that is located on the vessel support 18 and is connected to the U-valve 24. A supplying vessel 32 is connected through flexible tubing 30 to an injection fitting 34 which-matingly engages the injection port 21. A locking actuator 36 is employed to mate or clamp injection fitting 34 with injection port 21 and evacuation fitting 28 with through fitting 29.

FIG. 2A illustrates a presently preferred reaction vessel 10 in greater detail. The top stop cock 12 is preferably composed of a resilient material, such as Teflon, which permits penetration by a needle 38 that forms a part of the injection fitting 20 or may be operated by hand. The bottom stop cock 14 is also preferably composed of Teflon and operated by hand. With the bottom stopcock 14 open and U-valve 24 in its open horizontal position, the vessel 10 may be evacuated by suction from a receiving vessel, such as the vessel 26, or by gravity flow.

The injection fitting 20 is illustrated in greater detail in FIG. 2B. A top fitting seal 40 is preferably composed of Teflon. The seal 40 includes a channel 42 which provides a path through the seal 40 to the needle 38. In the preferred embodiment, the needle 38 may be fitted with a sprayer attachment with which to wash the inner surfaces of the vessel 10. A tapered end 44 fits within the inside diameter of the top vessel glass tube 13 and an annular shoulder 46 abuts the top of the glass tube 13. A tapered inlet 48 accepts the injection fitting 34. The seal 40 also includes a bleeding channel 50 which may be utilized to connect the interior of the vessel 10 to the ambient environment and relieves excess pressure within the vessel 10 during the filling process or as otherwise desired during system operation.

FIG. 2C illustrates the spring-loaded evacuation fitting 22 in greater detail. An inner sleeve 52 rests within an outer sleeve 54. An O-ring 56 is affixed to the top of the inner sleeve 52 and seals against the outside diameter of the vessel's bottom glass tube 15. A spring 58 is located between the inner sleeve 52 and outer sleeve 54 and provides constant pressure between the tapered bottom of the glass tube 15 and a tapered inlet 60 of the inner sleeve 52. In this manner, both the inner sleeve 52 and O-ring 56 seal the fitting 22 against the glass tube 15. Additionally, since the fitting 22 is spring-loaded, the vessel 10 may be easily removed and replaced without leakage.

Figure 3B:
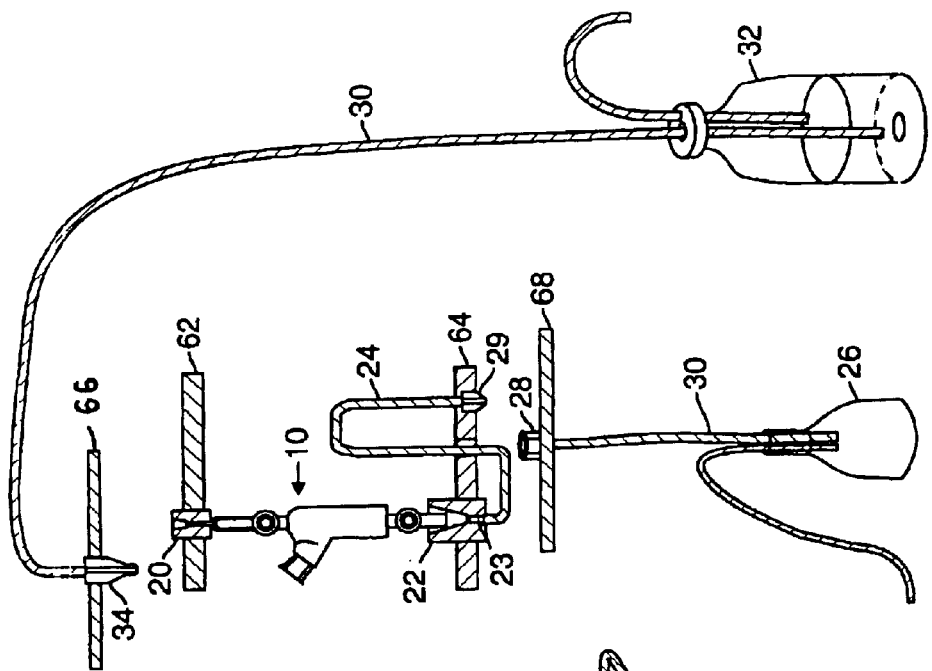
FIGS. 3A, 3B and 3C are illustrative views, respectively, of a reaction vessel with its fittings engaged, with its fittings disengaged, and with a U-valve opened.
Figure 3C:
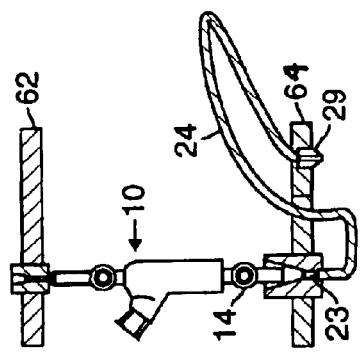
Figure 3A:
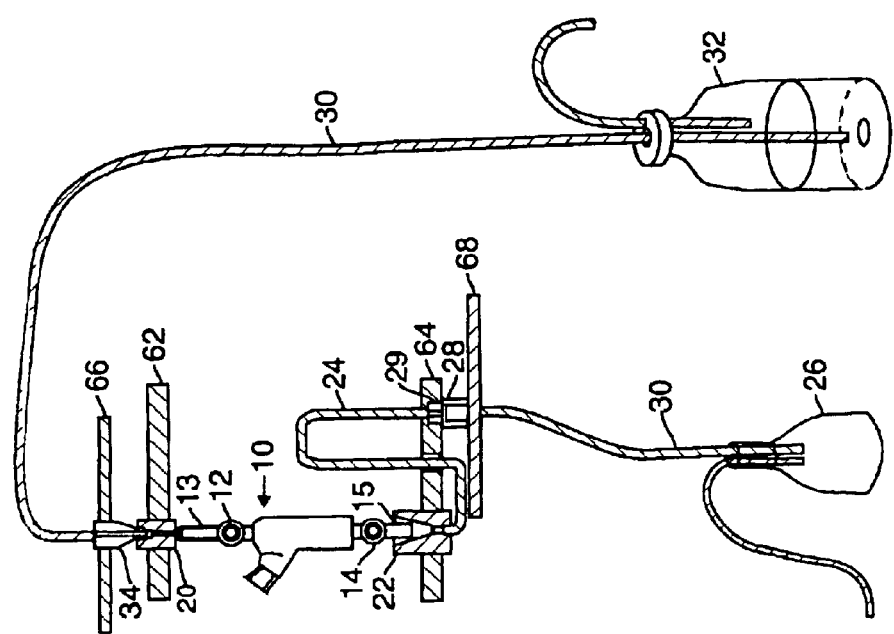

FIG. 3A illustrates aspects of a presently preferred embodiment of a reaction optimization tool in accordance with the present invention. In this embodiment, upper 62 and lower 64 carousel plates, respectively include the injection fittings 20 and evacuation fittings 22. As will be illustrated in greater detail in relation to the discussion of FIG. 4, an injection carousel 66 and a evacuation carousel 68 house the injection fittings 34 and evacuation fittings 28, respectively.

In FIG. 3A, the injection 66 and evacuation carousels 68 are shown in the closed or clamped position, that is, with the injection 34 and evacuation 28 fittings engaged with the injection 21 and evacuation 23 ports, respectively. Although the evacuation fitting 28 and evacuation port 23 are engaged, they are engaged indirectly, through the fitting 29 and U-valve 24.

The injection carousel 66 and evacuation carousel 68 are shown separated in FIG. 3B, thus disengaging the respective injection fitting 34 and port 21 and evacuation fitting 28 and port 23. With the U-valve 24 in the illustrated vertical U-shaped position shown in FIG. 3B, fluid will not flow from the vessel 10 into the U-valve to a higher level than the fluid level within the vessel 10. Therefore, no fluids from within the vessel 10 will flow through the evacuating fitting 28 unless, as illustrated in FIG. 3C, the flexible tubing from which the U-valve 24 is made is bent over to a horizontal position so that sufficient head pressure is provided to force fluid through the valve 24. Bending the tubing of U-valve 24 may be accomplished by pulling on a cord attached to the valve, by pushing on a rod attached to the valve 24, by rotating U-valve 24 against a properly shaped camming surface, or the like. To close the U-valve 24, the tubing is allowed or forced to return to its neutral, closed position illustrated in FIGS. 3A and 3B.

Figure 4:
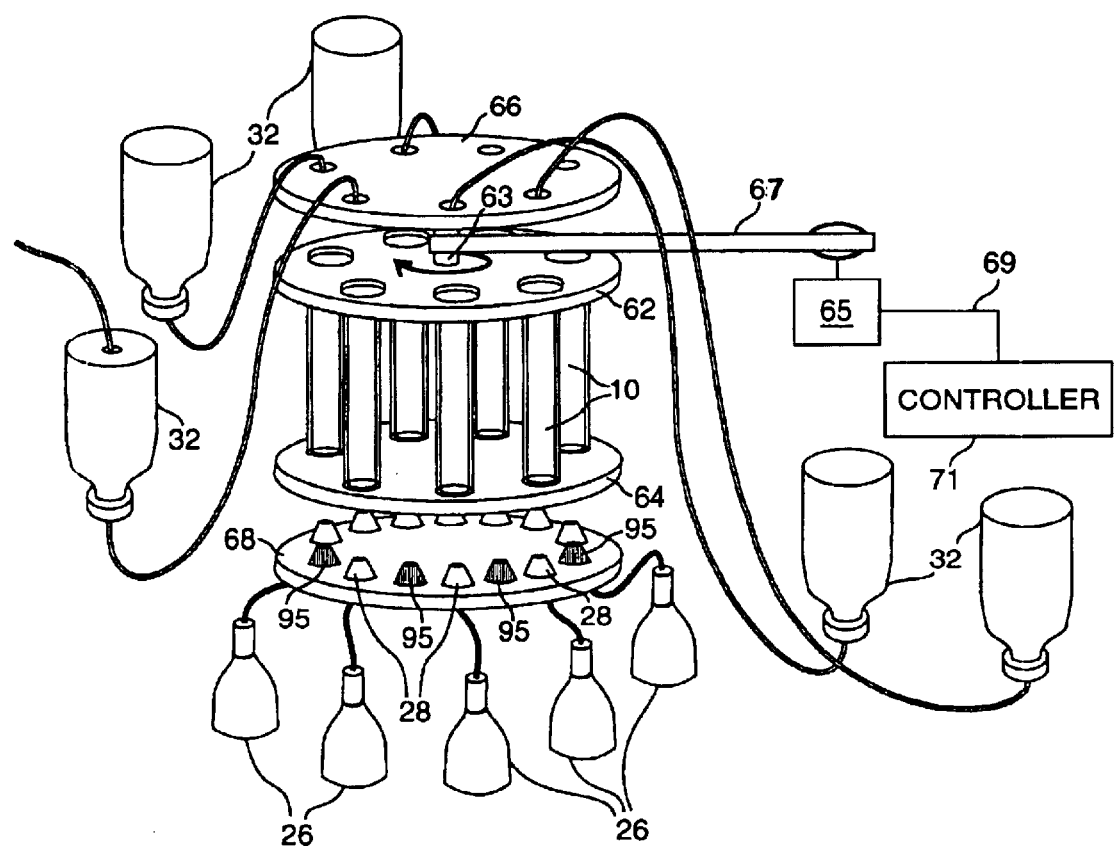
FIG. 4 is a perspective view of a carousel embodiment of the present invention.

The perspective view of FIG. 4 illustrates a presently preferred universal solvent exchanger, with some components eliminated for the sake of clarity. The reaction vessels 10 are arranged in a circular manner between the upper 62 and lower 64 carousel plates. This carousel combination, including the fittings, which are not shown in this drawing, is supported by a framework in a conventional manner. A stepper motor 65 is attached to the combination through a timing belt 67 which rotates a shaft 63 which, in turn, causes the carousel combination to rotate through a desired angle subject to either manual or program control. It will be recognized that any suitable programmed computer and drive circuitry may be employed, and that while a stepper motor and timing belt are shown, rotation may be controllably caused utilizing any suitable motor, a Geneva mechanism, a rack and pinion drive, a pneumatic actuator or other known drive mechanisms.

In any case, the appropriate fittings and vessels are controllably rotated when the injection 66 and evacuation 68 plates are disengaged to the appropriate position as shown in FIG. 4. The plates 66 and 68 may be controlled by a clamping mechanism or actuator such as the actuator 36 of FIG. 1 or any of a variety of alternative actuators which may suitably control the positions of these plates. The stepper motor 65 of FIG. 4 is connected through electrical wires 69 to a controller 71, which is preferably a microprocessor based controller. The controller 71 controls the operation of motor 65 subject to stored program control. While rotation is principally employed to position the vessels for fluid exchange, it will be recognized that back and forth rotation of the carousel may be employed to cause mixing of the components in the vessels 10. The actuator may also be designed to vibrate or shake the carousel.

After appropriately aligning the vessels as discussed above, the injection 20 and evacuation ports 22 may be aligned and engaged with any of the respective injection 34 and evacuation 28 fittings located below them. Blocking fittings 95 are shown interleaved with the evacuation fittings 28 on the evacuation carousel housing 68. Engagement with the blocking fittings 95 further ensures that no liquid will exit the bottom of the reaction vessels 10 when the contents of the vessels are agitated, for example, by rotating, vibrating or moving the upper and lower carousel plates 62 and 64 or when the vessels and their seals are under a pressure which could cause leakage. It will also be recognized that top blocking fittings may also suitably be employed for pressurized reactions and the like. In this way, liquid may be delivered to and evacuated from any vessel in any sequence desired, under program control. For example, chemical reagents may be added, solvents may be added and drained, washing solution may be flowed through the vessel, and a host of other liquids may be controllably flowed in and out of the vessel as desired. Thus, the present invention provides universal fluid exchange while avoiding complex tubing and control arrangements and also while avoiding cross contamination.

Figure 5B:
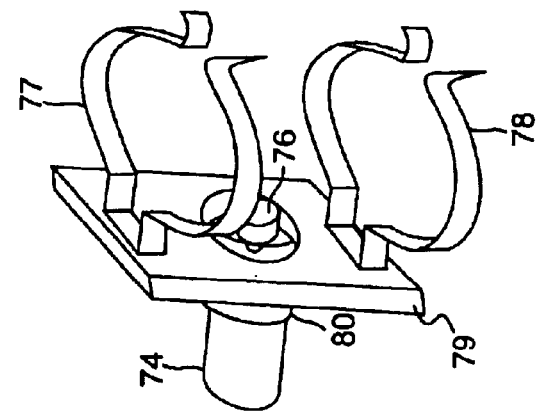
FIG. 5B illustrates an integral stirrer motor and heater mount.
Figure 5A:
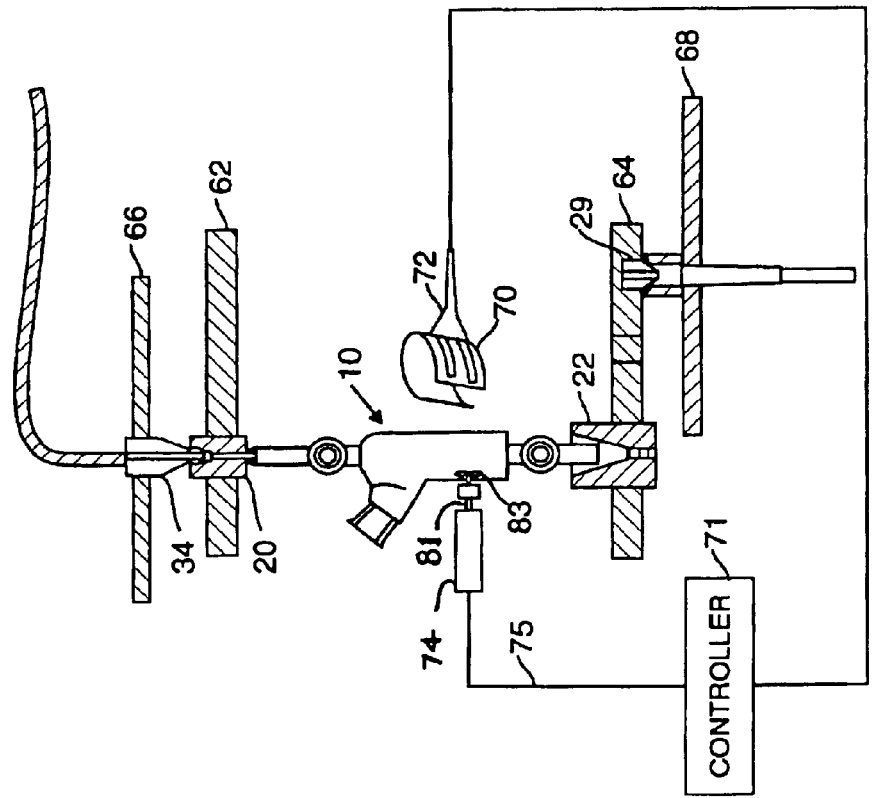
FIG. 5A is a partial view of a reaction vessel/carousel combination such as the one illustrated in FIG. 4 that additionally includes an individually controllable side stirring device and snap-on vessel heater in accordance with another aspect of the present invention.

Each reaction vessel 10 may also be fitted with a snap-on heating collar 70, as illustrated in FIG. 5A. In the preferred embodiment, the heating collar includes a resistive heater such as flexible heating pads with positive temperature coefficient of resistance ("TCR") available from Minco Products, Inc. of Minneapolis, Minn. which allows for on-line individual control when controlled by their HEAT-ERSTAT™ controllers based on the known or expected heating profile of each vessel 10. Two wires 72 provide both power and temperature sensing for the heater 70. As power is applied to the heater 70, the temperature of the heater increases and the resistance of the heater's resistive material changes. The controller 71 supplies power through wires 72 to the heater 70 and can detect this change in resistance and thereby determine the heater's temperature. By knowing the heating profile in the vessel 10 in response to the temperature of the heater 70, the reaction temperature may be suitably controlled without the need for a thermocouple or some other sensor located inside the vessel 10. This approach avoids possible sensor corrosion and eliminates cleaning and other contamination problems. The controller 71 can cut off power when the desired reaction temperature is reached. The collar 70 preferably includes a blanket of Silicon rubber insulation on the side of the collar which does not come in contact with the vessel 10. This insulation ensures that the bulk of the power supplied to the collar 70 is used to heat reactants contained within the vessel 10.

The heater 70 may also include a spring mounting arrangement suitable to clamp the heater in place. As shown in FIG. 5B, it is presently preferred to employ a dual spring comprising two separated bands 77 and 78 attached to a small platform or bracket 79 which joins those spring clamps and simultaneously provides a mount for a stirring motor bracket 80. The preferred flexible TCR heating pad is not shown in FIG. 5B so other details can be seen; however, it would preferably be wrapped like a partial three-quarter or seven-eighth cylinder against the inner curves of the bands 77 and 78, and have a small cutout for magnet 76. Existing spring holders, such as those typically employed as holders for electrolytic capacitors, broom holders, cable and pipe holders, and the like may be employed as the bands 77 and 78. The bands 77 and 78 simply snap around the vessel or vessels 10 holding the heater 70 and motor 74 in place.

Alternatively, a simple metallic collar may be employed as shown in FIG. 5A. This collar would support the heater's resistive material on one side and the insulation material on the other and, in its neutral position, would fit snugly over the reaction vessel, but is flexible enough to slip around the vessel while still being resilient enough to return to its neutral position after slipping around the vessel. As an alternative to the TCR heating material, a bimetal switch such as those available from Warren G-V Industries, a unit of General Signal Incorporated located in Whippany, N.J., may be mounted on the reaction vessel 10 and electrically connected in series with a simple resistive heating coil. When the switch reaches a predetermined temperature, it opens the electrical path to the heater 70. Switches having various activation temperatures are available and heater/switch combinations could be color coded according to the desired activation temperature.

FIGS. 5A and 5B also illustrate a stirring motor 74 which has a magnet 76 mounted on a shaft 81. The motor 74 is connected through electrical wires 75 to the controller 71 which selectively controls the supply of power to the motor 74 under program control. Alternatively, an operator may key in the identification of vessels to be stirred, as well as other pertinent data such as how fast and how long the stirring should be performed.

The motor 74 may be conventionally mounted on a hinged arm (not shown), which positions the magnet near the outer wall of the reaction vessel 10. A bushing such as the bushing 80 of FIG. 5B is preferably employed to provide a small but constant air gap of approximately 0.05 inches between the magnet and the vessel wall to prevent scratching of the vessel while providing strong rotational force to rotate a stirring bar 83 located within the reaction vessel 10. The stirring bar 83 is attracted to the magnet on the shaft of the motor 74 with sufficient force to be attracted to the wall of the vessel, where it spins about an axis perpendicular to the axis of the vessel 10 and creates a vortex starts about the same axis and then bends upwards. Since the stirring bar is located on the side wall of the reaction vessel 10, fewer of the microscopic beads used in chemical synthesis, such as combinatorial chemical synthesis, will be ground up during the stirring process. By contrast, using a conventional bottom stirrer, the weight and force of a spinning stirring bar tends to grind up such beads against the bottom of the vessel or a frit where the vessel is equipped with a frit. Stirring also helps to ensure fast and even heat distribution throughout the vessel.

Figure 6A:
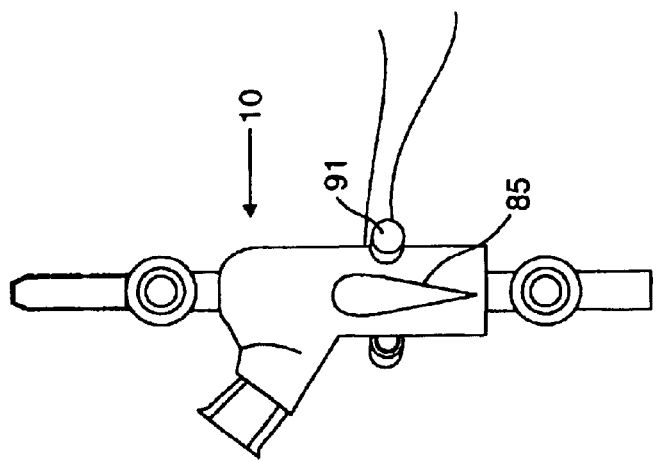
FIG. 6A illustrates a reaction vessel, including a stirrer in accordance with another aspect of the present invention.

An alternative, bottom stirrer 85 is shown within the reaction vessel 10 of FIG. 6A. The stirrer 85 is formed like a tapered wire whisk. Its narrow end rests on the bottom of the reaction vessel 10. Electromagnetic push-pull coils 91 provide a varying magnetic field to the stirrer in a conventional manner causing the stirrer 85 to rotate within the vessel 10. The stirrer 85 and coils 91 are illustrated in somewhat greater detail in FIG. 6B.

Figure 6B:
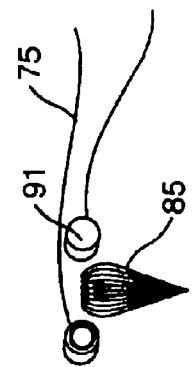
FIG. 6B is a more detailed view of the stirrer of FIG. 6A.
Figure 7B:
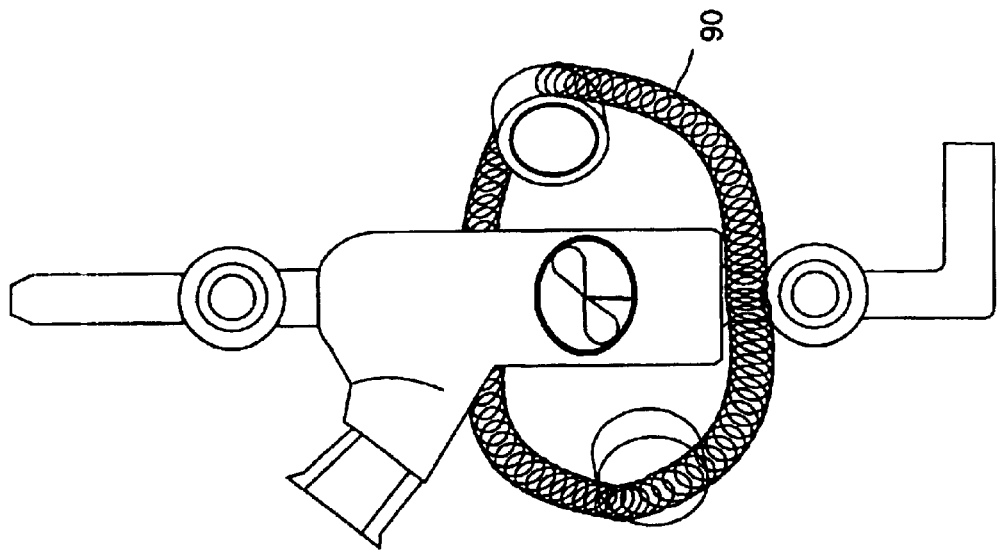
FIG. 7B illustrates drive coils for driving a stirrer such as the stirrer of FIG. 7A.
Figure 7A:
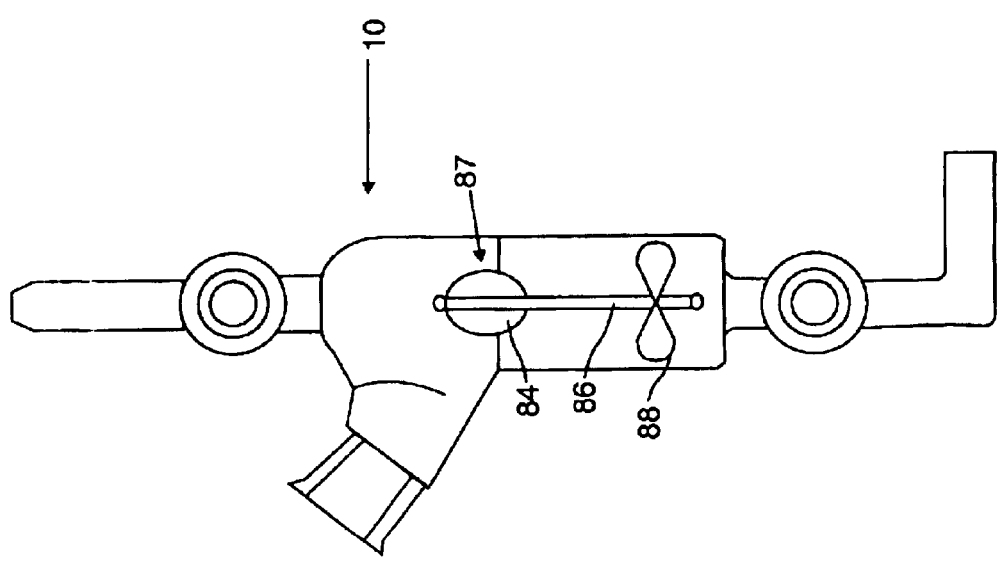
FIG. 7A is a sectional view of a reaction vessel, with a floating stirrer enclosed therein.

FIG. 7A illustrates an alternative floating stirrer 87 which floats within the reaction vessel 10. The stirrer 87 includes a float 84 mounted on one end of a shaft 86, with vanes 88 of ferrous material mounted on the other end of the shaft 86. Push pull magnetic coils such as the coils 91 of FIGS. 6A and 6B provide a varying magnetic field to the vanes 88, thereby causing the floating stirrer to agitate material within the vessel 10. Since the stirrer 87 floats in the reaction vessel, few if any of the microscopic beads used in combinatorial chemical synthesis will be ground up during the stirring process.

FIG. 7B illustrates further details of suitable magnetic coils 90 for driving the stirrers. While push-pull coils present a very simple implementation, a set of coils arranged around a vessel, as shown in FIG. 7B, which can be selectively turned on and off will allow the creation of rotating, reciprocating and crossing magnetic fields for varied stirring patterns, and improved control.

Figure 8:
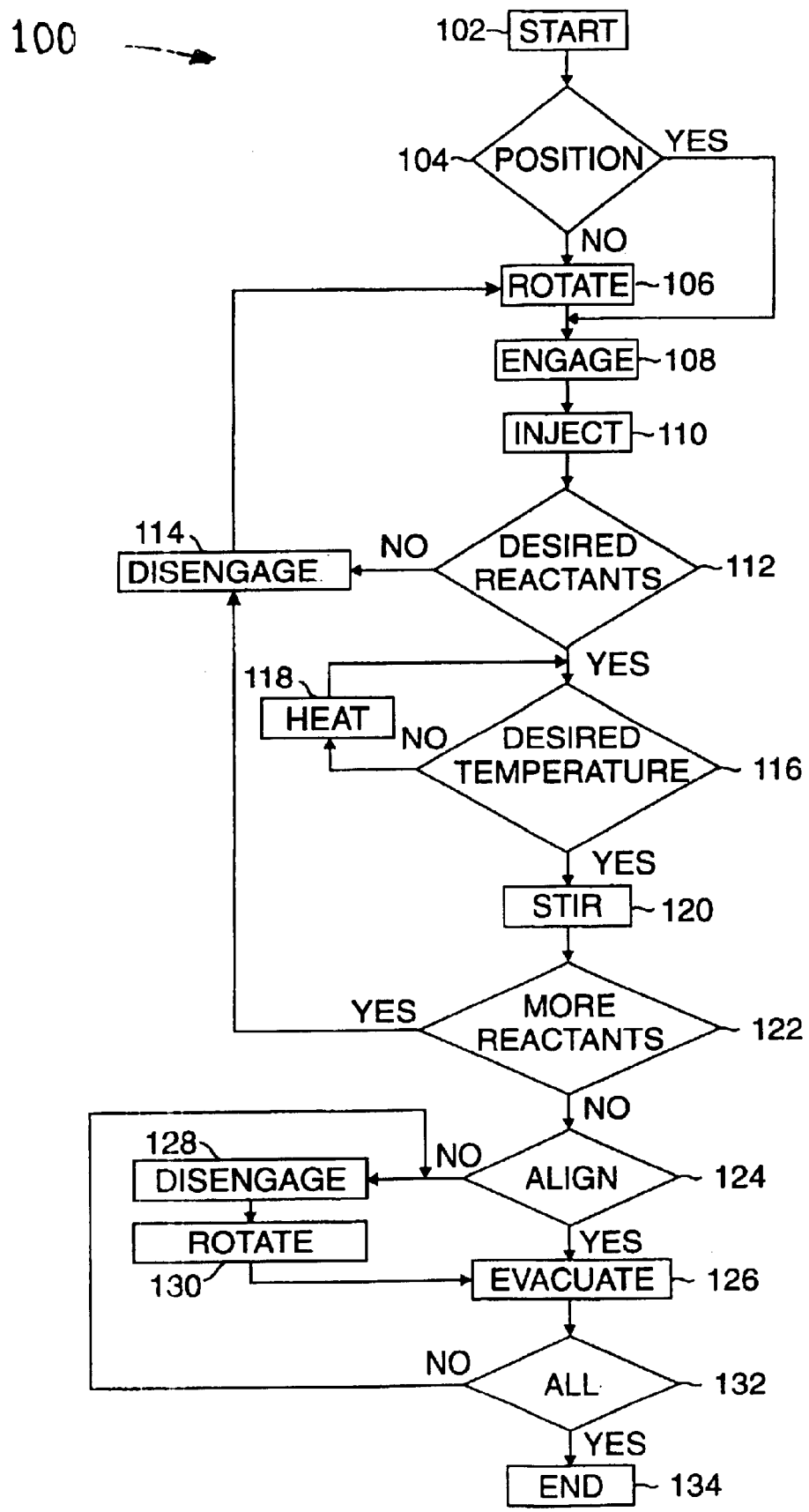
FIG. 8 illustrates a method of providing universal fluid exchange in accordance with the present invention.

The flowchart of FIG. 8 depicts a preferred method 100 of providing universal fluid exchange to combine reactants in one or more reaction vessels, to control the temperature of the reactants, to mix the reactants, and to evacuate the reaction products into the desired receiving vessels. These operations are preferably carried out under control of the controller 71. The flow chart provides a general description of the controller's stored program operation. The following example will assume that the controller 71 is effecting this process under stored program control. It is also assumed that the injection and evacuation fitting carousels 66 and 68 are not engaged with the reaction vessel carousel plates 62 and 64 initially.

The process begins at step 102 and proceeds to step 104, where the controller 71 determines whether a vessel 10 of interest is in a desired location, that is one in which it is able to receive the appropriate reactant from a supplying vessel 32. An optical sensor or sensors may be employed to make this determination. If the vessel 10 of interest is not properly positioned, the process proceeds to step 106, where the controller 71 rotates the vessel support carousel, comprising plates 62 and 64, until the vessel of interest is aligned with the injection fitting 34 of interest. Alternatively, the process can begin by aligning a desired vessel with the supply for any vessel having fluid that it is desired to direct to that vessel.

The process proceeds to step 108, where the fitting carousel plates 66 and 68 are moved into engagement with the vessel support carousel. This is also the step to which the process proceeds from step 104 should the controller determine in step 104 that the vessel is positioned as desired.

Once the injection and evacuation carousel plates are thus engaged, the process proceeds to step 110 where a desired fluid, such as a reactant or solvent is injected into one or more vessels of interest. After injection, the process moves to decision block 112 wherein the controller determines whether all the reactants and/or solvents necessary for this stage of the reactions are now contained within all the vessels 10. If not, the process moves to step 114, where the injection 66 and evacuation 68 carousel plates are disengaged and, from there, to step 106 where the vessel support carousel is again rotated into position.

On the other hand, if all the desired reactants are contained in all the vessels 10, the process proceeds to decision block 116 where the controller 71 determines whether the reactants within the reaction vessels 10 are at the desired temperature or temperatures and, if not, proceeds to step 118 where heat is applied for some period of time determined by the controller 71.

When the vessels' temperatures are acceptable, or alternatively, as heat is being supplied, the process proceeds to step 110 where the controller stirs the reactants. After stirring, the controller 71 determines whether more reactants are required for any of the reactions taking place in any of the reaction vessels 10, as represented by the decision block 122. If more reactants are required, the process moves to step 114 and on from there as previously described. If no more reactants are required, the controller may proceed to step 124, where it determines which of the reaction vessels 10 are aligned with the desired receiving vessels 26 and evacuates the contents of those vessels 10. For those vessels 10 that are not aligned with the desired receiving vessels 26, the controller 71 proceeds to step 128 and then to step 130, where it disengages the fitting plates 66 and 68 and rotates the vessel support carousel to a desired position, then to step 126, where reactants are evacuated into appropriate receiving vessels 26. Alternatively, the vessels 10 may be manually removed. Evacuation may also be employed with fluids such as solvents, washes, tagging solutions and the like.

In the decision block 132, the controller 71 determines whether all reaction vessels 10 have been evacuated and, if they have, proceeds to end step 134. On the other hand, if more vessels 10 must be evacuated, the controller 71 proceeds from step 132 to step 128 and proceeds as previously described.

The foregoing description of specific embodiments of the invention has been presented for the purposes of illustration and description. It is not intended to be exhaustive or to limit the invention to the precise forms disclosed, and many modifications and variations are possible in light of the above teachings. For example, while the present invention has been disclosed principally in the combinatorial chemistry context, it will be recognized that its teachings may be generally applicable to parallel synthesis, tagging and tag washing, solvent exchangers, bead washers and the like. Further, the reaction vessel supports need not be circular carousels. Linear arrangements of vessels are also contemplated, and would utilize appropriate translation or reciprocation means. The reaction vessel/carousel combination could be stationary, with the fitting carousels rotated into position to engage with the desired vessel. The presently disclosed embodiments were chosen to describe and explain the principles of the invention and its practical application, to thereby enable others skilled in the art to best utilize the invention. It is intended that the scope of the invention be limited solely by the claims appended hereto.

We claim:

1. A combinatorial chemical synthesis reaction tool, comprising:

a plurality of reaction vessels adapted for chemical synthesis, a reaction vessel support disposed to hold the plurality of reaction vessels in a preferred orientation, a plurality of injection ports, each injection port including a pressure seal, situated to provide access to one of said reaction vessels, the plurality of injection ports operable for the injection of liquids into said reaction vessels, a plurality of evacuation ports, each evacuation port including a pressure seal, situated to provide access to one of said reaction vessels, the plurality of evacuation ports operable for the evacuation of fluids from said reaction vessels, and a plurality of injection fittings and evacuation fittings formed to matingly engage said respective injection and evacuation ports and to thereby enable the simultaneous delivery of fluids to the reaction vessels or the simultaneous evacuation of fluids from said reaction vessels, and an actuator for changing the relative orientations of the reaction vessel support and the plurality of injection fittings and evacuation fittings, so as to selectively align a given injection fitting and evacuation fitting with a different one of said reaction vessels.

2. The reaction tool of claim 1, wherein said injection port is located at the top of said reaction vessel.

3. The reaction tool of claim 2, wherein said evacuation port is located at the top of said reaction vessel.

4. The reaction tool of claim 2, wherein said evacuation port is located at the bottom of said reaction vessel.

5. The reaction tool of claim 1, further comprising:

a supplying vessel, and flexible tubing connected directly from said injection fitting to said supplying vessel.

6. The reaction tool of claim 5, further comprising:
a receiving vessel, and
flexible tubing connected directly from said evacuation fitting to said receiving vessel.

7. The reaction tool of claim 1, wherein said evacuation port is a spring-loaded port.

8. The reaction tool of claim 1, wherein said reaction vessel support comprises:
top and bottom vessel support plates with tapered injection through fittings.

9. The reaction tool of claim 8 further comprising an actuator to selectively control movement of the top and bottom vessel support plates.

10. The reaction tool of claim 1, further comprising:
a stirring motor with a magnet attached to its shaft, said magnet positioned adjacent a sidewall of said reaction vessel; and
a stirring bar located within said reaction vessel, said stirring bar tending to follow the rotation of said magnet.

11. The reaction tool of claim 1, further comprising:
electromagnetic coils mounted around the outside of said reaction vessel, and
a tapered whisk stirrer located within said reaction vessel, said stirrer being responsive to varying magnetic fields produced by said coils by rotating within said reaction vessel, thereby stirring the contents of said vessel.

12. The reaction tool of claim 1, further comprising:
electromagnetic push-pull coils mounted adjacent the outside of said reaction vessel, and
a floating stirrer located within said reaction vessel said stirrer being responsive to varying magnetic fields produced by said push-pull coils by rotating within said reaction vessel, thereby stirring the contents of said vessel.

13. The reaction tool of claim 1, further comprising:
a resistive heater which snaps on to the exterior of said reaction vessel.

14. The reaction tool of claim 13, wherein said resistive heater includes means for selective on-line control.

15. The reaction tool of claim 1, further comprising a U-valve formed of flexible tubing and connected to regulate the flow of liquids from said evacuation through fitting.

16. A combinatorial chemical synthesis reaction tool for providing fluids to a plurality of chemical synthesis reaction vessels, comprising:
a reaction vessel support adapted to hold the plurality of reaction vessels in a preferred orientation,
an injection port, including a pressure seal, situated to provide access to each one of the reaction vessels for the injection of liquids into said reaction vessels,
an evacuation port, including a pressure seal, situated to provide access to each one of the reaction vessels for the evacuation of fluids from said reaction vessel,
a plurality of injection fittings and evacuation fittings formed to matingly engage said respective injection and evacuation ports and to thereby enable the simultaneous delivery of fluids to the reaction vessels or the simultaneous evacuation of fluids from said reaction vessels, and
an actuator for changing the relative orientations of the reaction vessel support and the plurality of injection fittings and evacuation fittings, so as to selectively align a given injection fitting and evacuation fitting with a different one of said reaction vessels.

17. The reaction tool of claim 16 further comprising the plurality of reaction vessels and wherein at least one of the reaction vessels comprises:
an enclosed vessel having a first inlet and a second inlet disposed proximately to a first end thereof, and an outlet disposed proximately to a second end thereof;
a first stopcock disposed within the first inlet; and
a second stopcock disposed within the outlet, said at least one reaction vessel adapted for ready insertion and removal from the reaction vessel support.

18. The reaction tool of claim 17 wherein the reaction vessel further comprises:
means for preventing solid phase material from escaping from the reaction vessel via the outlet while allowing fluid to flow through the outlet.

19. The reaction vessel of claim 18 wherein said means comprises a first frit disposed within the vessel at the second end thereof so as to prevent solid phase materials from escaping from the vessel via the outlet.

20. The reaction vessel of claim 19 wherein the distance between the first frit and the outlet is less than the thickness of the first frit.

21. The reaction vessel of claim 17 further comprising means for preventing solid phase material from escaping from the reaction vessel via the first inlet, while allowing fluid to enter the vessel via the first inlet.

22. The reaction vessel of claim 19 further comprising a second frit disposed within the first inlet.

23. The reaction vessel of claim 17 wherein the reaction vessel comprises glass.

24. The reaction vessel of claim 23 wherein the glass is strengthened adjacent to said outlet.

25. The reaction vessel of claim 17 wherein the outlet extends at an angle from a central axis extending lengthwise through the reaction vessel.

26. The reaction vessel of claim 25, wherein said angle is less than or equal to ninety degrees.

27. The reaction vessel of claim 25 wherein the second inlet extends at an angle from a central axis extending lengthwise through the reaction vessel.

28. The reaction vessel of claim 17 wherein the second inlet comprises a ground upper section adapted to receive a stopper therein thereby sealing the second inlet.

29. The reaction vessel of claim 17 wherein the second inlet comprises a threaded end adapted to receive a threaded cap.

30. The reaction vessel of claim 20 wherein the threaded end or cap comprises Teflon.

31. The reaction vessel of claim 17 wherein said vessel is enclosed by an outer hollow shell comprising an outer wall and an inner wall defining a liquid tight space therebetween.

32. The reaction vessel of claim 31 further comprising a fluid inlet adapted to allow fluid to flow within said hollow shell, and a fluid outlet adapted to allow fluid to flow out of said hollow shell.

33. The reaction tool of claim 16 further comprising the plurality of reaction vessels and wherein at least one of the reaction vessels comprises:
an enclosed vessel having a first inlet and a second inlet disposed proximately to a first end thereof, and an outlet disposed proximately to a second end thereof:
a first stopcock disposed within the first inlet;
a second stopcock located within the outlet; and
an outer hollow shell surrounding the interior reaction volume of the reaction vessel, said at least one reaction vessel adapted for ready insertion and removal from the reaction vessel support and custom fitting said support.

34. The reaction toot of claim 33 wherein the reaction vessel further comprises:

means for allowing fluid to flow through said outer hollow shell.

35. A universal fluid exchanger comprising:

a plurality of reaction vessels;

a reaction vessel support disposed to hold the plurality of reaction vessels in a preferred orientation, the reaction vessel support further comprising top and bottom carousel vessel support plates with tapered injection through fittings formed in a ring around the periphery of said top carousel vessel support plate and tapered evacuation fittings formed in a matching ring around the periphery of said bottom vessel support carousel plate;

a plurality of injection ports, each injection port including a pressure seal, situated to provide access to one of said reaction vessels, the plurality of injection ports operable for the injection of liquids into said reaction vessels;

a plurality of evacuation ports, each evacuation port including a pressure seal, situated to provide access to one of said reaction vessels, the plurality of evacuation ports operable for the evacuation of fluids from said reaction vessels;

a plurality of injection fittings and evacuation fittings formed to matingly engage said respective injection and evacuation ports and to thereby enable the delivery of fluids to the reaction vessels and the evacuation of fluids from said reaction vessels; and an actuator for changing the relative orientations of the reaction vessel support and the plurality of injection fittings and evacuation fittings, so as to selectively align a given injection fitting and evacuation fitting with a different one of said reaction vessels.

36. The fluid exchanger of claim 35, further comprising:

a top carousel fitting plate with fittings arranged in a ring around the periphery of said top carousel fitting plate to match the tapered injection through fittings of said top carousel vessel support plate.

37. The fluid exchanger of claim 36, further comprising:

a bottom carousel fitting plate with fittings arranged in a ring around the periphery of said bottom carousel fitting plate to match the tapered evacuating through fittings of said bottom carousel vessel support plate.

38. The fluid exchanger of claim 37, wherein said top and bottom carousel fitting plates close to simultaneously engage the injection fittings of said carousel top fitting plate with the tapered injection through fittings of said top carousel vessel support plate and to simultaneously engage the evacuation fittings of said bottom carousel fitting plate with the tapered through fittings of said bottom carousel vessel support plate.

39. The fluid exchanger of claim 38, wherein said actuator is connected to said vessel support carousel causing it to rotate under control of a motor to thereby align fittings and through fittings in a desired manner when said fitting plates are disengaged.

40. The fluid exchanger of claim 34, wherein said supplying vessels are connected to supply reagents and solvents for use in combinatorial chemical synthesis.

41. The fluid exchanger of claim 40, wherein the actuator further compriese a carousel rotation motor connected to rotate said vessel support carousel; and said fluid exchanger further comprises:

a resistive heater which snapes on to the exterior of said reaction vessel, a stirring motor with a magnet attached to its shaft, said magnet positioned at the sidewall of said reaction vessel; and a controller connected to control said carousel rotation motor, said resistive heater and said stirring motor.

42. The fluid exchanger of claim 41, further comprising:

a plurality of reaction vessels, each having a resistive heater snapped on to its exterior; and A plurality of stirring motors positioned at the sidewalls of said reaction vessels, with each resistive heater and each stirring motor connected for stored program control by said controller.

* * * * *